United States Patent [19]

Parsons et al.

[11] 4,414,221
[45] Nov. 8, 1983

[54] PESTICIDAL 1,2,4-TRIAZOLE COMPOUNDS

[75] Inventors: John H. Parsons, Saffron Walden; Peter J. West, Cambridge, both of England

[73] Assignee: FBC Limited, Cambridge, England

[21] Appl. No.: 246,042

[22] Filed: Mar. 20, 1981

[30] Foreign Application Priority Data

Mar. 22, 1980 [GB] United Kingdom ............... 8009769

[51] Int. Cl.³ .................... A01N 43/64; A01N 43/82; C07D 249/08; C07D 249/12
[52] U.S. Cl. ................. 424/269; 260/453.4; 260/453.5; 424/250; 424/251; 424/272; 544/179; 544/242; 544/315; 544/336; 544/406; 548/131; 548/132; 548/133; 548/262; 548/263; 548/265; 548/266; 548/269; 564/74; 564/271
[58] Field of Search ................. 548/262; 424/269

[56] References Cited

U.S. PATENT DOCUMENTS 4,097,599 6/1978 Evans et al. ............... 548/262
4,151,169 4/1979 Sale et al. ............... 548/262

OTHER PUBLICATIONS

Elderfield, Heterocyclic Compounds, vol. 7, (New York, 1961), pp. 438–439.

*Primary Examiner*—Alton D. Rollins
*Attorney, Agent, or Firm*—Morgan, Finnegan, Pine, Foley & Lee

[57] ABSTRACT

The compounds of the formula:

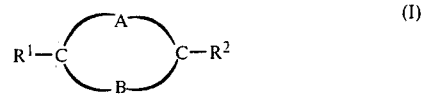

wherein $R^1$ represents phenyl substituted in at least the 2-position by fluorine, chlorine, bromine or iodine, $R^2$ represents a group $R^3$, $-OR^3$, $-SR^3$ or $-NR^3R^4$ where $R^3$ represents hydrogen, alkyl of 1 to 6 carbon atoms, cycloalkyl of 3 to 7 carbon atoms, alkenyl of 2 to 6 carbon atoms, cycloalkenyl of 3 to 7 carbon atoms, alkynyl of 2 to 6 carbon atoms, phenyl, phenylalkyl of 7 to 10 carbon atoms or naphthyl, each of which may be unsubstituted or substituted by one or more halogen atoms, alkyl or alkoxy or alkylthio groups of 1 to 6 carbon atoms, nitro groups, cyano groups or mercapto groups, $R^4$ represents a group as defined for $R^3$ but not necessarily identical thereto, and A and B, together with the carbon atoms to which they are attached, form a 3,6-disubstituted pyridazine, a 3,6-disubstituted dihydropyridazine, a 2,5-disubstituted pyrimidine, a 1,2,4-oxadiazole, a 1,2,4-oxadiazoline or a 1,2,4-triazole ring, and the quaternary salts thereof, are novel compounds which are pesticidal, notably with respect to acarids, insects and aphids and their eggs and larvae. Compositions containing the compounds are also described as well as processes for their preparation and methods of using them.

6 Claims, No Drawings

PESTICIDAL 1,2,4-TRIAZOLE COMPOUNDS

This invention concerns new heterocyclic compounds which are pesticidal, notably with respect to acarids, insects and aphids and their eggs and larvae.

In one aspect, this invention provides a method of combating pests, especially acarids, insects or aphids, and their eggs and larvae, which comprises applying to a site either infested or liable to infestation with them an effective amount of one or more compounds of the formula:

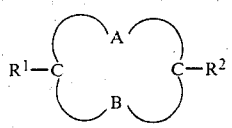 (I)

wherein $R^1$ represents phenyl substituted in at least the 2-position by fluorine, chlorine, bromine or iodine, $R^2$ represents a group $R^3$, $-OR^3$, $-SR^3$ or $-NR^3R^4$ where $R^3$ represents hydrogen, alkyl of 1 to 6 carbon atoms, cycloalkyl of 3 to 7 carbon atoms, alkenyl of 2 to 6 carbon atoms, cycloalkenyl of 3 to 7 carbon atoms, alkynyl of 2 to 6 carbon atoms, phenyl, phenylalkyl of 7 to 10 carbon atoms or naphthyl, each of which may be unsubstituted or substituted by one or more halogen atoms, alkyl or alkoxy or alkylthio groups of 1 to 6 carbon atoms, nitro groups, cyano groups or mercapto groups, $R^4$ represents a group as defined for $R^3$ but not necessarily identical thereto, and A and B, together with the carbon atoms to which they are attached, form a 3,6-disubstituted pyridazine, a 3,6-disubstituted dihydropyridazine, a 2,5-disubstituted pyrimidine, a 1,2,4-oxadiazole, a 1,2,4-oxadiazoline or a 1,2,4-triazole ring, and the quaternary salts thereof.

In another aspect, the invention provides per se the compounds of formula I, with the exception of 3,5-bis(2-chlorophenyl)-1,2,4-oxadiazole.

The group $R^1$ is very preferably mono-substituted only, specific preferred groups being 2-fluorophenyl, 2-chlorophenyl and 2-bromophenyl, 2-chlorophenyl being especially preferred.

$R^2$ preferably represents a group $R^3$, especially a cycloalkyl group of 5 or 6 carbon atoms, e.g. cyclohexyl, or a phenyl group which is desirably substituted by one or more halogen atoms, C 1 to 4 alkyl or alkoxy groups or nitro groups. Where the group $R^2$ represents such a substituted phenyl group, it is preferably mono-substituted, particularly by halogen, specific preferred groups being 2-chlorophenyl, 2-fluorophenyl, 2-bromophenyl, 2-iodophenyl, 2-methylphenyl, 3-methylphenyl and 4-methylphenyl.

When $R^3$ and/or $R^4$ represents alkyl of 1 to 6 carbon atoms, it may, for example, be methyl, ethyl, n-propyl, isopropyl or, especially, t-butyl. Preferred alkenyl and alkynyl groups which $R^3$ and $R^4$ may represent include vinyl, allyl and propargyl. When $R^3$ and/or $R^4$ represents alkyl, cycloalkyl, alkenyl, cycloalkenyl or alkynyl, it is preferably unsubstituted. When substituted, however, it is preferably substituted by one or more halogen atoms, cyano groups or hydroxy groups, specific preferred substituted groups being trifluoromethyl, chloromethyl, cyanomethyl, trichloromethyl and 2-hydroxyethyl.

When $R^3$ and/or $R^4$ represents a phenylalkyl group, it is preferably benzyl which is desirably unsubstituted or mono-substituted by halogen, e.g. 2-chlorobenzyl or 4-chlorobenzyl.

When $R^3$ and/or $R^4$ represents naphthyl it may be a 2-naphthyl group, but is more preferably a 1-naphthyl group. It is desirably unsubstituted. When substituted, however, it is preferably substituted by halogen or by a hydroxy group or a methoxy group, e.g. 2-hydroxy-1-naphthyl, 2-methoxy-1-naphthyl or 4-methoxy-1-naphthyl.

When $R^2$ represents a group $-SR^3$ or $-NR^3R^4$, specific preferred groups include methylthio, cyclohexylthio, methylamino, cyclohexylamino, dimethylamino, phenylamino and benzylamino.

$R^1$ and $R^2$ are preferably identical.

The heterocyclic ring represented by A, B and the carbon atoms to which they are attached may be further substituted if desired in any available position, for example by one or more groups R, where R represents an alkyl group of 1 to 6 carbon atoms, an alkenyl group of 2 to 6 carbon atoms, a phenyl group, a phenylalkyl group of 7 to 10 carbon atoms, an alkoxycarbonyl group of 2 to 6 carbon atoms, or an acyl group (e.g. an alkanoyl group of 2 to 6 carbon atoms), each of which may be unsubstituted or substituted by one or more halogen atoms, hydroxy groups, cyano groups or alkoxy groups of 1 to 4 carbon atoms.

Specific preferred compounds of formula I include:
3,5-bis(2-chlorophenyl)-1-methyl-1,2,4-triazole, and the salts thereof;
3,5-bis(2-chlorophenyl)-1-ethyl-1,2,4-triazole, and the salts thereof;
3,5-bis(2-chlorophenyl)-1-allyl-1,2,4-triazole, and the salts thereof;
3-(2-chlorophenyl)-5-(2-fluorophenyl)-1-methyl-1,2,4-triazole, and the salts thereof;
2,5-bis(2-chlorophenyl)pyrimidine;
3,6-bis(2-chlorophenyl)-4-phenyl-pyridazine;
3,6-bis(2-chlorophenyl)-4-isopropylpyridazine; and
3,6-bis(2-chlorophenyl)-4-methoxycarbonylpyridazine.

In a further aspect, this invention provides a pesticidal, especially an acaricidal, larvicidal or ovicidal, composition which comprises one or more compounds of formula I as defined hereinbefore in association with a suitable carrier and/or surface active agent.

The compounds of formula I may be prepared by a number of methods depending principally on the nature of the ring formed by A and B and the carbon atoms to which they are attached.

The 3,6-disubstituted pyridazines of formula I may be prepared by reaction of a corresponding tetrazine of the formula:

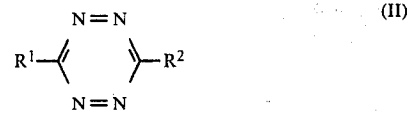 (II)

wherein $R^1$ and $R^2$ are as defined hereinbefore with:

(a) a substituted acetylene of the formula $R^8C\equiv CH$ where $R^8$ represents a group as defined hereinbefore for $R^2$, or (b) a ketone of the formula $R^8COCH_2R^9$ where $R^9$ represents a group as defined hereinbefore for $R^2$.

In each case, the product is, where $R^8$ and/or $R^9$ is other than hydrogen, a pyridazine substituted at the 3- and 6-positions by groups $R^1$ and $R^2$, and in the 4- and/or 5-positions by groups $R^8$ and $R^9$ as appropriate.

The reaction (a) is preferably effected in an inert solvent, e.g. an aromatic hydrocarbon such as xylene or an ether such as tetrahydrofuran, anisole or dioxan, and conveniently at a temperature of from 0° to 150° C., preferably 100° to 150° C. Reaction (b) is preferably base catalysed using, for example an alkali-metal hydride, hydroxide amide or alkoxide, e.g. potassium hydroxide, sodamide or sodium hydride as the base. The reaction is conveniently effected in a suitable solvent medium, for example an alkanol such as methanol or ethanol, or an ether such as dioxan or tetrahydrofuran, and at a temperature of from 0° to 25° C.

The dihydro-3,6-disubstituted pyridazines of formula I may be prepared by a process analogous to process (a) above, wherein a substituted ethylene of the formula $R^8CH=CH_2$ is employed instead of the substituted acetylene.

The 1,2,4-triazoles of formula I may be prepared by a process in which a substituted azine of the formula:

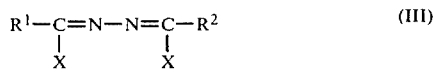

wherein $R^1$ and $R^2$ are as defined hereinbefore and each X represents a leaving group is reacted with ammonia or an amine of formula $RNH_2$ where R is as defined hereinbefore, to give the desired compound.

Where an amine is employed, the product is of course a 1,2,4-triazole substituted in the 4-position by the group R.

The reaction is conveniently carried out at an elevated temperature, e.g. from 30° to 100° C., especially 50° to 80° C., in an appropriate solvent medium, e.g. an alkanol, e.g. ethanol, an ether, e.g. tetrahydrofuran, or a hydrocarbon, e.g. toluene.

X preferably represents halogen (especially chlorine or bromine), cyano, or C 1 to 4 alkoxy (especially methoxy).

The compounds of formula III may be prepared by methods known per se.

The 1,2,4-triazoles of formula I wherein $R^2$ represents a group $R^3$ or $SR^3$ may be prepared by reaction of a 4-aminotriazole of the formula:

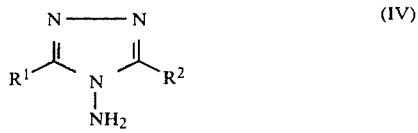

wherein $R^1$ is as defined hereinbefore and $R^2$ represents a group $R^3$ or $SR^3$, or a quaternary derivative thereof with nitrous acid to give the desired compound.

Where the compound of formula IV is a quaternary triazolium derivative, the product triazole is of course substituted on the 1- or 2-position.

The nitrous acid is preferably generated in situ by the reaction of an alkali-metal nitrite and an acid, and the reaction is desirably effected at a temperature of from 0° C. to 20° C.

The quaternary derivatives of the compounds of formula V may be prepared by conventional techniques from the unquaternised compounds of formula IV.

The compounds of formula IV may be prepared by conventional processes.

The 1,2,4-triazoles of formula I wherein $R^2$ represents a group $R^3$ may alternatively be prepared by reaction of a compound of the formula:

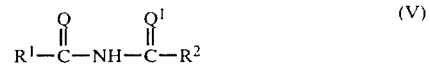

where $R^1$ is as defined hereinbefore, $R^2$ represents a group $R^3$, and Q and $Q^1$, which may be the same or different, each represent O, S or NH, with a hydrazine of the formula $R^aNHNH_2$ where $R^a$ represents hydrogen or a group R as defined hereinbefore to give the desired compound.

Where $R^a$ is other than hydrogen, the compound produced is a 1,2,4-triazole substituted in the 1-position by the group $R^a$.

The reaction is conveniently carried out at a temperature of from 0° to 50° C., preferably 20° to 30° C., and in a suitable solvent medium, e.g. an alkanol such as methanol or ethanol or an ether such as dioxan.

The compounds of formula V used as starting materials may themselves be prepared by a process in which a thioamide of the formula

is reacted with a suitable acyl halide of the formula $R^2CQ^1Hal$, where Hal represents hydrogen, especially chlorine or bromine.

The reaction is desirably effected in the presence of a base, especially an organic base, e.g. pyridine, and at a temperature of from 0° to 30° C.

The 1,2,4-triazoles of formula I wherein $R^2$ represents a group $-OR^3$ or $-NR^3R^4$ may be prepared from the corresponding 2-imino-1,3,4-oxadiazoles of the formula:

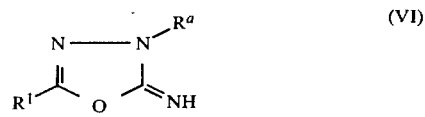

where $R^1$ and $R^a$ are as defined hereinbefore by reaction thereof with a suitable alcohol $R^2OH$ or amine $R^3R^4NH$ in the presence of a base to give the desired compound.

The reaction is a base-catalysed condensation, and is desirably effected at a temperature of from 50° to 150° C., preferably 50° to 100° C. The base employed may be any convenient inorganic base, e.g. sodium or potassium hydroxide.

The 1,2,4-triazoles of formula I wherein $R^2$ represents a group $-SR^3$ may be prepared by oxidatively cyclising a compound of the formula:

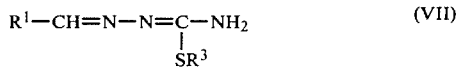

or an acid addition salt thereof in the presence of a base to give the desired compound.

The oxidising agent employed is preferably a mild oxidising agent which does not affect the remainder of the molecule. Suitable oxidising agents include ferric chloride and lead tetra-acetate.

The base is preferably an anhydrous inorganic base, e.g. potassium hydroxide, and the reaction is desirably effected at a temperature of from 50° to 150° C.

The compounds of formula VII may themselves be prepared by a process in which an isothiosemicarbazide of the formula:

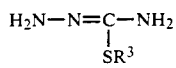

$$H_2N-N=C-NH_2 \quad\quad (VIII)$$
$$\quad\quad\quad |$$
$$\quad\quad\quad SR^3$$

or an acid addition salt thereof is condensed in a suitable solvent medium with an aldehyde of the formula $R^1CHO$ where $R^1$ is as defined hereinbefore.

The solvent is desirably a polar solvent, e.g. an alkanol, such as ethanol. The reaction is desirably effected at a temperature of from 20° to 80° C.

The 1,2,4-triazoles of formula I which are unsubstituted at the 1-position may, if desired, be converted into 1-substituted 1,2,4-triazoles of formula I, for example by alkylation or aralkylation by methods known per se.

The 1,2,4-oxadiazoles of formula I may be prepared by a process in which an amidoxime of the formula:

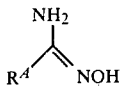

is reacted with an acid halide of the formula $R^BCOHal$ (where Hal represents halogen and $R^A$ and $R^B$ represent the pair of groups $R^1$ and $R^2$) to give the desired compound.

The reaction is desirably effected in a suitable solvent medium, especially an aprotic solvent such as dioxan, and with heating to a temperature of 50° to 120° C., preferably 80° to 110° C.

The amidoximes of formula IX and the acid halide may themselves be prepared by methods analogous to those employed for the preparation of related compounds.

The 1,2,4-oxadiazolines of formula I may be prepared by a process in which an amidoxime of formula IX is reacted with an aldehyde of formula $R^BCHO$.

The reaction is desirably effected in a suitable solvent medium, especially an aprotic solvent such as toluene, and with heating to a temperature of 50° to 150° C., preferably 80° to 120° C.

The pyrimidines of formula I may be prepared by a process in which a compound of the formula:

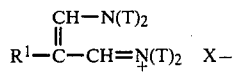

$$\quad\quad CH-N(T)_2 \quad\quad (X)$$
$$\quad\quad ||$$
$$R^1-C-CH=\overset{+}{N}(T)_2 \quad X-$$

where $R^1$ is as defined hereinbefore, each T represents alkyl or aryl, and $X^-$ represents an anion is reacted with a compound of the formula:

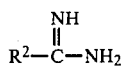

$$\quad NH \quad\quad (XI)$$
$$\quad ||$$
$$R^2-C-NH_2$$

where $R^2$ is as defined hereinbefore, to give the desired compound.

The reaction is preferably effected in the presence of a base, e.g. sodium methoxide, and in a suitable solvent, e.g. an alkanol such as methanol, and conveniently at an elevated temperature, e.g. 20° to 100° C.

The quaternary salts of the compounds (especially the 1,2,4-triazoles) of formula I may be prepared from the free compounds of formula I by reaction with a suitable alkylating agent.

The compounds of formula I are of general use as insecticides, acaricides, aphicides, larvicides and/or ovicides. They are of particular use against the eggs and larvae of acarids, particularly the eggs of the red spider mite, *Tetranychus cinnabarinus*, but also against the eggs and larvae of other mite and tick species, e.g. *Tetranchus urticae, Panonychus ulmi, Phyllocoptrata oleivora, Eutetranychus banksi, Panonychus citri* and *Tetranychus MacDanieli* in crops, and cattle tick (Boophilus), sheep tick (Ixodes), soft tick (Rhipicephalus), and poultry mites, in domestic and farm animals. Aphids against which the compounds of formula I are active include bean aphids (*Megoura viciae* and *Aphis fabae*), peach-potato aphids (*Myzus persicae*), bird-cherry aphid (*Rhopalosiphum padi*), cabbage aphid (*Brevicoryne brassicae*), green apple aphid (*Aphis pomi*), and hop aphid (*Phorodon humuli*).

The compounds are normally employed in the form of compositions.

The compositions of the invention will normally be produced initially as formulations containing from 0.5 to 99%, preferably from 0.5 to 85% by weight, more usually from 10 to 50% by weight, of the active compounds, which are diluted if necessary before application to the locus to be treated such that the concentration of active ingredient in the formulation applied is, for application to crops, from 0.05 to 5% by weight, or, for application to animals, from 100 to 1000 ppm.

The compounds of formula I are generally water insoluble and may be formulated in any of the ways commonly adopted for insoluble compounds.

For example, they may be dissolved in a water immiscible solvent, for example a high boiling hydrocarbon (e.g. xylene), as carrier, suitably containing dissolved emulsifying agents so that the composition acts as a self-emulsifiable oil on addition to water.

The compounds may alternatively be admixed with a wetting agent with or without a solid carrier to form a wettable powder which is soluble or dispersible in water, or may be mixed with just a solid carrier to form a solid product.

An aqueous suspension concentrate may alternatively be prepared by grinding the compounds with water, a wetting agent and a suspending agent (e.g. xanthan gum).

Solid carriers with which the active compounds may be incorporated include clays, sands, talc, mica or solid fertilizers, such products either comprising dust or larger particle size materials.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl tuarine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The composition may alternatively be in the form of an aerosol composition, suitably using a cosolvent and a wetting agent, in addition to the propellant, which is suitably a polyhalogenated alkane such as dichlorodifluoromethane.

The compositions according to the present invention may contain in addition to the active compounds of formula I other active insecticides, acaricides, ovicides, aphicides, bactericides and fungicides. It has been found that particular advantages are obtained with mixtures or sequences with other acaricides, especially those which combat the motile stages, e.g. amitraz, dicofol, cyhexatin or propargite, or other aphicides, e.g. pirimicarb, malathion, acephate, azinphos-methyl, chlorpyrifos, demephion, demeton-S-methyl, dimethoate, phenitrothion, formothion, heptenophos, oxydemeton-methyl or thiometon, and particularly where the compound of formula I is one of those mentioned specifically hereinbefore.

The method of combating acarids, their eggs or their larvae provided by the present invention may be employed at any site where infestations of such pests are present or are liable to occur. Thus, it may be employed for example on plants or the soil.

Plants which may be treated include food crops, for example, fruit trees and cereals, e.g. apples, pears, apricots, citrus fruits, maize, wheat or barley, beans, sugar beet, potatoes, carrots, greenhouse crops, e.g. peppers, tomatoes, cucumbers, melons or strawberries, and ornamentals.

In their various applications the compounds of formula I may be used at various rates; thus for example for the treatment of plants for the control of pests on plants the compounds are suitably applied at a rate of about 0.25–16 ounces per acre (17–1120 g per hectare) or at a concentration of 1 to 2000 ppm as appropriate, e.g. 100 to 1000 ppm, and preferably 0.5–4 ounces per acre (35–280 g per hectare). Normally the compounds will be applied to the foliage of plants, but systemic activity has also been observed when applied to the soil around the base of the plants.

The following Examples are given merely to illustrate the present invention. The temperatures given therein are in °C., and parts and percentages are by weight.

EXAMPLE 1

1-Methyl-3,5-bis(2-chlorophenyl)-1,2,4-triazole (a) 4-Amino-3,5-bis(2-chlorophenyl)-1,2,4-triazole 2,2α,α-Tetrachlorobenzalazine (34.6 g) was added portionwise to a refluxing solution of hydrazine hydrate (20.0 g) in ethanol (250 ml). Refluxing was continued for one hour, then the solution was filtered and evaporated to dryness. The residue was treated with water and the solid was filtered off and dried. On recrystallisation from toluene, 15.3 g of desired product, mp 168°–170° C. were obtained.

(b) 3,5-Bis(2-chlorophenyl)-1,2,4-triazole

The product of stage (a) (19.5 g) was dissolved in glacial acetic acid (100 ml) and was treated with sodium nitrite (4.4 g) in water (15 ml) at 10° C. The precipitated solid was filtered off, washed, dried and recrystallised from methanol to yield 9.7 g of desired product, mp 159°–160° C.

(c) 1-Methyl-3,5-bis(2-chlorophenyl)-1,2,4-triazole

The product of stage (b) (3.0 g) and sodium methoxide (0.57 g) were dissolved in methanol (75 ml) and treated with methyl iodide (1.3 g). After standing for 3 days the solution was evaporated to dryness, treated with water and extracted into dichloromethane. The extract was washed with water and dried. Evaporation yielded 0.8 g of a solid, mp 82°–85° C., which was recrystallised twice from petroleum ether (80°–100°).

Analysis: Found: C, 58.96 H, 3.22 N, 13.55%. Theory: C, 59.23 H, 3.65 N, 13.82%.

EXAMPLES 2–8

The following compounds were all prepared by methods analogous to that of Example 1:

2. 1-Ethyl-3,5-bis(2-chlorophenyl)-1,2,4-triazole, orange oil.
3. 1-Allyl-3,5-bis(2-chlorophenyl)-1,2,4-triazole, green oil.
4. 1-Benzyl-3,5-bis(2-chlorophenyl)-1,2,4-triazole, brown oil.
5. 1-(2-Phenylethyl)-3,5-bis(2-chlorophenyl)-1,2,4-triazole, brown oil.
6. 1-Methyl-3,5-bis(2-fluorophenyl)-1,2,4-triazole, mp 103° C.
7. 1-Methyl-3-(2-chlorophenyl)-5-(2-fluorophenyl)-1,2,4-triazole, mp 110°–112° C.
8. 1-Phenyl-3-(2-chlorophenyl)-5-(2-fluorophenyl)-1,2,4-triazole, mp 97° C.

EXAMPLE 9

4-Methyl-3,5-bis(2-chlorophenyl)-1,2,4-triazole

To refluxing methylamine (2.44 g) in ethanol (50 ml), bis (α:2-dichloro-benzylidene)hydrazine (6.0 g) was added portionwise. The mixture was refluxed for 30 minutes, then poured into water (150 ml) and allowed to stand. The solid which formed was filtered off and recrystallised from toluene to give 2.5 g of desired product, mp 140° C.

EXAMPLES 10–12

The following compounds were all prepared by methods analogous to that of Example 9:

10. 4-Ethyl-3,5-bis(2-chlorophenyl)-1,2,4-triazole, mp 192° C.
11. 4-n-Propyl-3,5-bis(2-chlorophenyl)-1,2,4-triazole, mp 166° C.
12. 4-Allyl-3,5-bis(2-chlorophenyl)-1,2,4-triazole, mp 116° C.

EXAMPLE 13

1-Methyl-5-ethyl-3-(2-chlorophenyl)-1,2,4-triazole (a) 2-Chlorophenylthioamide

O-Chlorobenzonitrile (100 g) and triethylamine (73.4 g) were dissolved in pyridine (130 ml), and hydrogen sulphide was passed through the solution for 16 hours. It was then left to stand for 16 hours and was poured into ice/water (3 liters). The solid which formed was filtered off, dried in vacuo and recrystallised from toluene to give 66.5 g, mp 58°–59° C., of desired product.

(b) N-propanoyl-2-chlorophenylthioamide

The product of stage (a) (17.2 g) and pyridine (15.8 g) were dissolved in dry acetone (100 ml), and this solution was added dropwise with stirring to a solution of propanoyl chloride (18.5 g) in dry acetone (100 ml). The mixture was stirred for 5 minutes, pyridine hydrochloride was filtered off, and the filtrate was refluxed on a steam bath for 15 minutes. The reaction mixture was then poured into water (2 liters), and was allowed to stand overnight. The solid which formed was filtered off and recrystallised from cyclohexane, to yield 12.1 g of desired product, mp 65° C.

(c) 1-Methyl-5-ethyl-3-(2-chlorophenyl)-1,2,4-triazole

The product of stage (b) (10.7 g) was dissolved in dioxan (150 ml). Methylhydrazine (5.4 g) was added and the reaction mixture was stirred until the solution lost its colour. It was then left to stand for 15 minutes and was poured into water (1 liter). The product was then extracted into ether and dried over magnesium sulphate. The solvent was evaporated off and the residual oil was chromatographed on silica gel using dichloromethane as eluant. The fractions containing the desired product were evaporated down to yield 2.4 g of product, mp 44° C.

EXAMPLES 14–19

The following compounds were prepared by methods analogous to that of Example 13.
14. 5-Cyclohexyl-3-(2-Chlorophenyl)-1,2,4-triazole, mp 138°–140° C.
15. 1,5-Dimethyl-3-(2-chlorophenyl)-1,2,4-triazole, oil.
16. 1-Methyl-5-isopropyl-3-(2-chlorophenyl)-1,2,4-triazole, yellow/green oil.
17. 1-Methyl-5-cyclohexyl-3-(2-chlorophenyl)-1,2,4-triazole, mp 83° C.
18. 1-Methyl-5-m-tolyl-3-(2-chlorophenyl)-1,2,4-triazole, mp 95° C.
19. 1,5-Dimethyl-3-(2-fluorophenyl)-1,2,4-triazole, mp 66°–68° C.
20. 5-Methyl-3-(2,4-dichlorophenyl)-1,2,4-triazole, mp 153° C.

EXAMPLE 21

3-(2-Chlorophenyl)-5-benzylthio-1,2,4-triazole (a)

S-Benzyl-1-(2-chlorobenzylidene)isothiosemicarbazide hydrochloride

S-benzylisothiosemicarbazide hydrochloride (21.7 g) and 2-chlorobenzaldehyde were refluxed in ethanol (100 ml) for 30 minutes. The solid which precipitated was filtered off, washed with diethyl ether and dried on the filter to yield 34.0 g of desired product.

(b) 3-(2-Chlorophenyl)-5-benzylthio-1,2,4-triazole

The product of stage (a) (27.8 g) in ethanol (350 ml) was treated with sodium methoxide (4.4 g) on a steam bath. The mixture was then cooled and sodium chloride was filtered off. Ferric chloride (26.6 g) was then added and the mixture was stirred and refluxed for 6 hours before being evaporated down. The residue was dissolved in ether/water, and the mixture was separated. The ether layer was washed with water twice and with saturated brine once, and was dried over magnesium sulphate. On evaporation, 14.0 g of a brown oil product, mp 84°–86° C., were obtained.

EXAMPLES 22–23

The following compounds were prepared by methods analogous to that of Example 21:
22. 3-(2-Chlorophenyl)-5-ethylthio-1,2,4-triazole, mp 84°–86° C.
23. 3-(2-Chlorophenyl)-5-cyclopentylthio-1,2,4-triazole, mp 99°–102° C.

EXAMPLES 24–35

The following compounds were prepared from the corresponding 1-unsubstituted compounds by methods analogous to that of Example 1(c):
24. 1-Methyl-3-(2-chlorophenyl)-5-methylthio-1,2,4-triazole, yellow oil.
25. 1-Methyl-3-(2-chlorophenyl)-5-ethylthio-1,2,4-triazole, yellow oil.
26. 1-Methyl-3-(2-chlorophenyl)-5-n-propylthio-1,2,4-triazole, yellow oil.
27. 1-Methyl-3-(2-chlorophenyl)-5-isopropylthio-1,2,4-triazole, orange oil.
28. 1-Methyl-3-(2-chlorophenyl)-5-n-butylthio-1,2,4-triazole, yellow oil.
29. 2-Methyl-3-(2-chlorophenyl)-5-n-butylthio-1,2,4-triazole, yellow oil.
30. 1-Methyl-3-(2-chlorophenyl)-5-isobutylthio-1,2,4-triazole, orange oil.
31. 1(and 2)-Methyl-3-(2-chlorophenyl)-5-cyclopentylthio-1,2,4-triazole, orange oil.
32. 1(and 2)-Methyl-3-(2-chlorophenyl)-5-allylthio-1,2,4-triazole, mp 77°–80° C.
33. 1-Methyl-3-(2-chlorophenyl)-5-benzylthio-1,2,4-triazole, mp 75°–78° C.
34. 4-Methyl-5-(2-chlorophenyl)-3-mercapto-1,2,4-triazole, mp 124° C.
35. 4-Methyl-5-(2-chlorophenyl)-3-allylthio-1,2,4-triazole, mp 82° C.

EXAMPLE 36

1-Methyl-3-(2-chlorophenyl)-5-dimethylamino-1,2,4-triazole (a) 3-(2-Chlorophenyl)-5-amino-1,2,4-oxadiazole Cyanogen bromide (106 g) generated in situ by the reaction of bromine in methanol to aqueous sodium cyanide was added to o-chlorobenzhydrazide (170.5 g) and the mixture was stirred and refluxed for 6 hours. It was then evaporated and the solid was dissolved in aqueous methanol. Ammonium hydroxide was added to pH 7, then water was added to precipitate a solid which was filtered off and recrystallised from methanol to give a white solid product.

(b) 3-Methyl-5-(2-chlorophenyl)-2-imino-2,3-dihydro-1,3,4-oxadiazole

The product of stage (a) (3.9 g) and methylsulphate (2.5 g) were heated on a steam bath for 4 hours. The product was then triturated with ethyl acetate to give a white solid product.

(c) 1-Methyl-3-(2-chlorophenyl)-5-dimethylamino-1,2,4-triazole

The product of stage (b) (6.0 g), dimethylamine (1.8 g) and ethanol (50 ml) were refluxed for 50 hours. The mixture was then evaporated, poured into water, extracted with dichloromethane, washed, dried, evaporated and chromatographed to give a pale yellow oil product.

EXAMPLE 37

3-(2-Chlorophenyl)-5-n-butoxy-1,2,4-triazole

To the product of Example 36, stage (a), (9.7 g) in n-butanol (110 ml) was added potassium hydroxide (9.7 g), and the mixture was refluxed for 4 hours. It was then cooled, and excess potassium hydroxide was neutralised with acetic acid. The mixture was then evaporated to give 12.2 g of desired product.

EXAMPLE 38

1-Methyl-3-(2-chlorophenyl)-5-n-butoxy-1,2,4-triazole

By the method of Example 1(c) the above compound was prepared as a pale yellow oil (8.1 g) from the product of Example 37.

EXAMPLE 39

1-Methyl-3-(2-chlorophenyl)-5-ethoxy-1,2,4-triazole

By the method of Example 37 the above compound was prepared as a brown oil.

EXAMPLE 40

1,4-Dimethyl-3,5-bis(2-chlorophenyl)-1,2,4-triazolium methylsulphate

The product of Example 1 (15.0 g) and dimethyl sulphate (6.3 g) were heated at 150° C. for 30 minutes. The melt yielded, on crystallisation from petroleum, 20.4 g of desired product, mp 135°–140° C.

Analysis: Found: C, 47.34 H, 3.57 N, 9.65%. Required: C, 47.45 H, 3.98 N, 9.77%.

The triazoles of Examples 2–39 were also converted into corresponding quarternary salts by methods analogous to that described above.

EXAMPLE 41

3,6-Bis-(2-chlorophenyl)-4-phenylpyridazine 3,6-Bis(2-chlorophenyl)-1,2,4,5-tetrazine (4.6 g) and phenylacetaldehyde (2.0 g) were dissolved in tetrahydrofuran (60 ml). A solution of potassium hydroxide in methanol (1.5 ml, 1%) was added dropwise to the solution and left to stand for 5 minutes. The solution was evaporated to 20 mls volume and was then diluted with water (50 ml). The precipitated solid was filtered, washed with water and dried to give 5.5 g of desired product, mp 176°–178° C.

Analysis: Found: C, 69.70 H, 3.55 N, 7.05%. Theory: C, 70.04 H, 3.77 N, 7.43%.

EXAMPLES 42–43

The following compounds were prepared by methods analogous to that of Example 41:
42. 3,6-Bis(2-chlorophenyl)pyridazine, mp 169°–171° C.
43. 3,6-Bis(2-chlorophenyl)-4-isopropylpyridazine, brown oil.

EXAMPLE 44

3,6-Bis(2-chlorophenyl)-4-phenyl-4,5-dihydropyridazine

To styrene (2.34 ml) was added 3,6-bis(2-chlorophenyl)-1,2,4,5-tetrazine (2.6 g) in toluene (20 ml). The mixture was heated to reflux for 3 hours, and was then cooled. The solid which separated was filtered off and dried to yield 2.6 g of the desired product, mp 151°–153° C.

EXAMPLES 45–47

The following compounds were prepared by methods analogous to that of Example 44:
45. 3,6-Bis(2-chlorophenyl)-4-methoxycarbonyl-4,5-dihydropyridazine, mp 126°–125° C.
46. 3,6-Bis(2-chlorophenyl)-4-ethoxycarbonyl-4,5-dihydropyridazine, mp 138°–140° C.
47. 3,6-Bis(2-chlorophenyl)-4-dimethylamino-5,5-dimethyl-4,5-dihydropyridazine, mp 109°–110° C.

EXAMPLE 48

2,5-Bis(2-chlorophenyl)pyrimidine (a) N-[3-dimethylamino-2-(2-chlorophenyl)-2-propenylidene]-N-methylmethanaminium iodide Phosphoryl chloride (24.8 g) was added dropwise over 80 minutes to stirred dimethylformamide (20.3 g) at 0°–10° C. After stirring for a further hour, the mixture was allowed to warm to room temperature, and 2-chlorophenylacetic acid (9.23 g) was added portionwise over 15 minutes. The temperature of the stirred mixture was slowly raised over 1 hour to 95° C., and was held there for a further 8½ hours.

After cooling, the reaction mixture was added dropwise over 160 minutes to an ice-cold solution of potassium iodide (34.0 g) in water (54 ml). After stirring 3 hours at 0°–4° C., a brown solid was filtered off and washed with water. Purification by dissolution in hot ethanol, charcoaling, and trituration of the residue with ethyl acetate after evaporation gave 12.47 g of the desired product as a pale yellow crystalline solid, mp 262° C.

(b) 2,5-Bis(2-chlorophenyl)pyrimidine

Sodium methoxide (0.76 g) in methanol (20 ml) was added over 10 minutes to a stirred solution of N-[3-(dimethylamino)-2-(o-chlorophenyl)-2-propenylidene]-N-methylmethanaminium iodide (2.94 g) and o-chlorobenzamidine hydrochloride (2.31 g) in methanol (20 ml) at room temperature. The stirred mixture was refluxed for 2 hours and then poured into water (600 ml). It was then extracted with diethyl ether. The combined ether extracts were washed with 2 N hydrochloric acid, saturated brine, and were then dried. Evaporation gave a yellow solid which was purified by precipitation from ethanol with water. Filtration and drying in vacuo gave 2.22 g of 2,5-bis(2-chlorophenyl)pyrimidine as a pale yellow solid, mp 112° C.

Analysis: Found: C, 63.6 H, 3.8 N, 9.1%. $C_{16}H_{10}Cl_2N_2$ requires: C, 63.8 H, 3.35 N, 9.30%.

EXAMPLES 49-55

The following compounds were all prepared by methods analogous to that of Example 48:
49. 2,4-Bis(2-chlorophenyl)pyrimidine, mp 68°-69° C.
50. 4,6-Bis(2-chlorophenyl)pyrimidine, mp 126°-127° C.
51. 2-Cyclohexyl-4-(2-chlorophenyl)pyrimidine, yellow oil.
52. 2-Cyclohexyl-5-(2-chlorophenyl)pyrimidine, colourless oil.
53. 4-(2-Chlorophenyl)-2-benzylthiopyrimidine, colourless oil.
54. 4-(2-Chlorophenyl)-2-(2-chlorobenzylthio)pyrimidine, mp 69° C.
55. 4-(2-Chlorophenyl)-2-mercaptopyrimidine, mp 172°-174° C.

EXAMPLE 56

3,5-Bis(2-chlorophenyl)-1,2,4-oxadiazole

2-Chlorobenzoyl chloride (2.6 g) was dissolved in dioxan (90 ml) and 2-chlorobenzamidoxime (2.5 g) was added with stirring, followed by boron trifluoride etherate (0.2 ml). The solution was heated at reflux for 18 hours and was run down. The product was taken up in dichloromethane, and the solution was washed successively with saturated aqueous sodium bicarbonate, water, and saturated sodium chloride solution. It was then dried over magnesium sulphate, run down and recrystallised from ethanol to yield 2.3 g of desired product, mp 91°-92° C.

Analysis: Found: C, 58.11 H, 3.04 N, 9.93%. $C_{14}H_8Cl_2N_2O$ requires: C, 57.75 H, 2.77 N, 9.62%.

EXAMPLES 57-59

The following compounds were prepared by methods analogous to that of Example 56:
57. 3-(2-Chlorophenyl)-5-cyclohexyl-1,2,4-oxadiazole, pale yellow oil.
58. 3-(2-Chlorophenyl)-5-hydroxy-1,2,4-oxadiazole, mp 163°-165° C.
59. 5-(2-Chlorophenyl)-3-cyclohexyl-1,2,4-oxadiazole, yellow oil.

EXAMPLE 60

3,5-Bis(2-chlorophenyl)-4,5-dihydro-1,2,4-oxadiazole

2-Chlorobenzamidoxime (3.4 g), 2-chlorobenzaldehyde (2.8 g), p-toluenesulphonic acid (1 g) and toluene (100 ml) were heated to reflux for 16 hours in Dean and Stark apparatus. The solution was then run down, and the residue was recrystallised from methanol to give 1.4 g of desired product, mp 75°-78° C.

Analysis: Found: C, 56.95 H, 2.99 N, 9.4%. $C_{14}H_{10}Cl_2N_2O$ requires: C, 57.36 H, 3.44 N, 9.56%.

EXAMPLE 61

The following compound was prepared by a method analogous to that of Example 60:
61. 3-(2-Chlorophenyl)-5-cyclohexyl-4,5-dihydro-1,2,4-oxadiazole, mp 120°-123° C.

EXAMPLE 62

An emulsifiable concentrate formulation was prepared from the following ingredients:
Compound of Example 1: 100 g/l
Toximul D: 75 g/l
Toximul H: 25 g/l
Solvesso 200: to 1 liter Toximul D and Toximul H are anionic/non-ionic blends of emulsifiers. Solvesso 200 is a mixture of aromatic hydrocarbon fractions.

Analogous formulations were also prepared containing 5 and 15% by weight of the compound of Example 1.

EXAMPLE 63

A wettable powder formulation was prepared from the following ingredients:
Compound of Example 1: 40% w/w
Reax 45L: 5% w/w
Neosyl: 10% w/w
China clay: 45% w/w Reax 45L is a sodium lignosulphonate surfactant. Neosyl is a precipitated silica.

Analogous formulations were also prepared containing 10, 25 and 50% by weight of the compound of Example 1.

EXAMPLE 64

Formulations analogous to those of Examples 62 and 63 were prepared with the compounds of each of Examples 1, 2, 6, 7, 17, 56 and 60.

EXAMPLE A

Aqueous suspensions of the compounds listed below, together with 500 mg/liter of the ethylene oxide/nonylphenol wetting agent Synperonic NX per liter were applied to run-off to leaf discs cut from the leaves of French bean plants, *Phaseolus vulgaris*, each infested with 50-100 eggs of the greenhouse red spider mite, *Tetranychus cinnabarinus*.

The treated plants, together with controls treated with 500 mg/liter aqueous wetting agent alone were held at 22° C. for 7 days on moist filter paper. The percentage mortality of the mite eggs was then recorded and the $LC_{50}$ was determined and scored according to the following scale:

| $LC_{50}$ (ppm) | Score |
|---|---|
| >1000 | 0 |
| 300-1000 | 1 |
| 100-299 | 2 |
| 30-99 | 3 |
| 10-29 | 4 |
| 3-9.9 | 5 |
| <3 | 6 |

The results obtained were as follows:

| Ex No | Score | Ex No | Score |
|---|---|---|---|
| 1 | 6 | 42 | 3 |
| 2 | 6 | 44 | 3 |
| 3 | 5 | 45 | 2 |
| 6 | 2 | 47 | 4 |
| 7 | 5 | 55 | 2 |
| 39 | 5 | 56 | 2 |
| 40 | 2 | | |

EXAMPLE B

Aqueous suspensions containing 100, 50, 25, 10 and 5 mg of the compound of Example 1 per liter, together with 500 mg of the ethylene oxide-nonyl phenol wetting agent Synperonic NX per liter were applied to run-off to:

(a) young bean plants, Vicia fabae, which were then infested with 15 untreated adult viviparous female bean aphids, Megoura viciae;

(b) young bean plants, Vicia fabae, which were then infested with 20 untreated adult viviparous female black bean aphids, Aphis fabae;

(c) young chinese cabbage plants, Brassica spp which were then infested with 20 adult viviparous female peach-potato aphids, Myzus persicae.

The treated plants, together with controls treated with 500 g per liter aqueous wetting agent alone were held at 20° C. for 4 days under cylindrical plastic cages closed at the top with gauze. Surviving adult aphids were then removed and the plants, together with surviving young aphids, were held for a further 3 days.

The percentage reduction in aphid reproduction was assessed by comparing the number of live aphid nymphs on treated plants with the number on control plants. The reductions for the three species (a, b and c) were found to be as follows:

| Rate, mg/l | a | b | c |
|---|---|---|---|
| 100 | 100 | 100 | 100 |
| 50 | 100 | — | — |
| 25 | 100 | — | — |
| 10 | 100 | 100 | 94 |

| Rate, mg/l | a | b | c |
|---|---|---|---|
| 5 | 80 | 100 | 0 |

On the $LC_{50}$ scale set out in Example A the scores for this compound and for other compounds tested were as follows:

| Ex No | Score | Ex No | Score |
|---|---|---|---|
| 1 | 6 | 17 | 5 |
| 2 | 6 | 56 | 3 |
| 6 | 3 | 60 | 3 |
| 7 | 5 | | |

We claim:

1. A method of combating acarids, insects or aphids, or their eggs or larvae, which comprises applying to a site infested or liable to infestation therewith, an effective amount of one or more compounds of the formula:

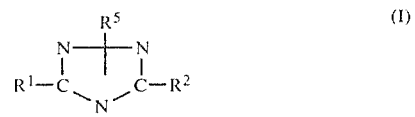

wherein $R^1$ represents phenyl substituted in the 2-position by fluorine, chlorine, bromine or iodine;

$R^2$ represents cycloalkyl of 3 to 7 carbon atoms, alkoxy of 1 to 6 carbon atoms, or phenyl substituted in the 2-position by halogen or by alkyl of 1 to 6 carbon atoms; and $R^5$ represents hydrogen, alkyl of 1 to 6 carbon atoms or alkenyl of 2 to 6 carbon atoms.

2. A method according to claim 1 wherein $R^1$ is 2-chlorophenyl.

3. A method according to claim 1 wherein $R^2$ represents cyclohexyl, 2-chlorophenyl, 2-bromophenyl or 2-fluorophenyl.

4. A method according to claim 1 wherein $R^5$ represents methyl, ethyl or allyl.

5. A method according to claim 1 wherein $R^5$ is in the 1-position on the triazole ring.

6. A method according to claim 1 wherein the compound of formula I employed is 3,5-bis(2-chlorophenyl)-1-methyl-1,2,4-triazole.

* * * * *